US00PP22612P2

(12) United States Plant Patent
Blom

(10) Patent No.: US PP22,612 P2
(45) Date of Patent: Mar. 27, 2012

(54) ***ECHINACEA* PLANT NAMED 'RASPBERRY TRUFFLE'**

(50) Latin Name: *Echinacea hybrida*
Varietal Denomination: Raspberry Truffle

(76) Inventor: Arie Blom, Oudewater (NL)

( * ) Notice: Subject to any disclaimer, the term of this patent is extended or adjusted under 35 U.S.C. 154(b) by 0 days.

(21) Appl. No.: 12/807,821

(22) Filed: Sep. 14, 2010

(51) Int. Cl.
*A01H 5/00* (2006.01)

(52) U.S. Cl. ..... Plt./428

(58) Field of Classification Search ..... Plt./428
See application file for complete search history.

*Primary Examiner* — Susan McCormick Ewoldt
(74) *Attorney, Agent, or Firm* — C. A. Whealy

(57) ABSTRACT

A new and distinct cultivar of *Echinacea* plant named 'Raspberry Truffle', characterized by its upright plant habit; freely basal branching habit; strong dark purple-colored stems and peduncles that are green in color and tinged with greyed purple; freely flowering habit; and large anemone-type inflorescences with light red-colored ray and disc florets.

3 Drawing Sheets

Botanical designation: *Echinacea hybrida.*
Cultivar denomination: 'RASPBERRY TRUFFLE'.

BACKGROUND OF THE INVENTION

The present invention relates to a new and distinct cultivar of *Echinacea* plant, botanically known as *Echinacea hybrida*, and hereinafter referred to by the name 'Raspberry Truffle'.

The new *Echinacea* plant is a product of a planned breeding program conducted by the Inventor in Vleuten and Zuidwolde, The Netherlands. The objective of the breeding program is to develop new freely branching and flowering *Echinacea* plants with attractive ray and disc floret coloration.

The new *Echinacea* plant originated from a cross-pollination conducted by the Inventor in July, 2006 in Vleuten, The Netherlands of a proprietary selection of *Echinacea hybrida* identified as code number Ec 201-001, not patented, as the female, or seed, parent with a proprietary selection of *Echinacea hybrida* identified as code number Ec 403-001, not patented, as the male, or pollen, parent. The new *Echinacea* plant was discovered and selected by the Inventor as a single flowering plant from within the progeny of the stated cross-pollination grown in a controlled environment in Zuidwolde, The Netherlands in July, 2008.

Asexual reproduction of the new *Echinacea* plant by micropropagation a controlled environment in Heerhugowaard, The Netherlands since July, 2008, has shown that the unique features of this new *Echinacea* plant are stable and reproduced true to type in successive generations.

SUMMARY OF THE INVENTION

Plants of the new *Echinacea* have been observed under all possible environmental conditions. The phenotype may vary somewhat with variations in environment such as temperature and light intensity, without, however, any variance in genotype.

The following traits have been repeatedly observed and are determined to be the unique characteristics of 'Raspberry Truffle'. These characteristics in combination distinguish 'Raspberry Truffle' as a new and distinct cultivar of *Echinacea* plant:

1. Upright plant habit.
2. Freely basal branching habit.
3. Strong stems and peduncles that are green in color and tinged with greyed purple.
4. Freely flowering habit.
5. Large anemone-type inflorescences with light red-colored ray and disc florets.

Plants of the new *Echinacea* can be compared to plants of the female parent selection. Plants of the new *Echinacea* differ from plants of the female parent selection in the following characteristics:

1. Plants of the new *Echinacea* are shorter than plants of the female parent selection.
2. Plants of the new *Echinacea* and the female parent selection differ in floret color as plants of the female parent selection have pink-colored ray and disc florets.
3. Plants of the new *Echinacea* and the female parent selection differ in stem and peduncle color as plants of the female parent selection have green-colored stems and peduncles.

Plants of the new *Echinacea* can be compared to plants of the male parent selection. Plants of the new *Echinacea* differ from plants of the male parent selection in the following characteristics:

1. Plants of the new *Echinacea* are shorter than plants of the male parent selection.
2. Plants of the new *Echinacea* have stronger branches than plants of the male parent selection.
3. Plants of the new *Echinacea* have larger inflorescences than plants of the male parent selection.

Plants of the new *Echinacea* can be compared to plants of *Echinacea hybrida* 'Pink Double Delight', disclosed in U.S. Plant Pat. No. 18,803. In side-by-side comparisons, plants of the new *Echinacea* differed from plants of 'Pink Double Delight' in the following characteristics:

1. Ray florets of plants of the new *Echinacea* were more upright than and not as drooping as ray florets of plants of 'Pink Double Delight'.
2. Plants of the new *Echinacea* and 'Pink Double Delight' differed in floret coloration as plants of 'Pink Double Delight' had dark pink-colored ray florets and darker pink-colored disc florets.

3. Plants of the new *Echinacea* and 'Pink Double Delight' differed in stem and peduncle color as plants of 'Pink Double Delight' had green-colored stems and peduncles.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet comprises a side perspective view of a typical flowering plant of 'Raspberry Truffle' grown in a container.

The photograph on the second sheet is a close-up view of a typical inflorescence of 'Raspberry Truffle'.

The photograph on the third sheet is a close-up view of the upper surface of a typical leaf of 'Raspberry Truffle'.

DETAILED BOTANICAL DESCRIPTION

The aforementioned photographs and following observations and measurements describe plants grown during the summer in an outdoor nursery in Zuidwolde, The Netherlands and under conditions and practices which approximate those generally used in commercial *Echinacea* production. During the production of the plants, day temperatures ranged from 15° C. to 32° C. and night temperatures ranged from 8° C. to 18° C. Measurements and numerical values represent averages for typical flowering plants. Plants were six months old when the photographs and description were taken. In the following description, color references are made to The Royal Horticultural Society Colour Chart, 2007 Edition, except where general terms of ordinary dictionary significance are used.

Botanical classification: *Echinacea hybrida* 'Raspberry Truffle'.

Parentage:

*Female parent.*—Proprietary selection of *Echinacea hybrida* identified as code number Ec 201-001, not patented.

*Male parent.*—Proprietary selection of *Echinacea hybrida* identified as code number Ec 403-001, not patented.

Propagation:

*Type.*—By micropropagation.

*Time to initiate roots, summer.*—About one week at 25° C.

*Time to produce a rooted young plant, summer.*—About five weeks at 21° C.

*Root description.*—Fine, fibrous; pale cream in color.

*Rooting habit.*—Freely branching; moderately dense.

Plant description:

*Plant form/growth habit.*—Herbaceous perennial; upright and columnar plant habit, broad inverted triangle; freely basal branching habit; low vigor to moderately vigorous growth habit.

*Plant height.*—About 42.7 cm.

*Plant diameter or spread.*—About 43.6 cm.

*Basal branches.*—Length: About 36.5 cm. Diameter: About 4 mm. Internode length: About 3.4 cm. Aspect: About 30° from vertical. Strength: Strong. Texture: Pubescent, strigose; rough. Color: Close to 146B to 146C tinged with close to 183A and 184A.

Foliage description:

*Arrangement.*—Alternate, simple.

*Length.*—About 8.1 cm.

*Width.*—About 4.3 cm.

*Shape.*—Ovate.

*Apex.*—Acute.

*Base.*—Attenuate to cuneate.

*Margin.*—Slightly serrated, shallow serrations.

*Texture, upper and lower surfaces.*—Pubescent, strigose; rough.

*Venation pattern.*—Pinnate.

*Color.*—Developing leaves, upper surface: Close to N137B. Developing leaves, lower surface: Close to 137C. Fully expanded leaves, upper surface: Close to 137B; venation, close to 144B to 144C. Fully expanded leaves, lower surface: Close to 137C; venation, close to 145C.

*Petioles.*—Length: About 6 cm. Diameter: About 4 mm. Texture, upper surface: Smooth, glabrous. Texture, lower surface: Pubescent, strigose; rough. Color, upper surface: Close to 144B to 144C. Color, lower surface: Close to 144B.

Inflorescence description:

*Appearance.*—Rotate anemone-type inflorescence form with ray and disc florets arranged acropetally on a capitulum; inflorescences positioned upright above the foliar plane on strong peduncles.

*Quantity of inflorescences per plant.*—About eleven.

*Fragrance.*—None detected.

*Time to flower.*—Plants flower continuously from early July to late September in The Netherlands.

*Inflorescence longevity.*—Inflorescences maintain good substance for about three weeks on the plant; inflorescences not persistent.

*Inflorescence bud.*—Height: About 1.3 cm. Diameter: About 1.5 cm. Shape: Flattened globular. Color: Close to 146C.

*Inflorescence size.*—Diameter: About 7.1 cm. Depth (height): About 4.2 cm. Disc diameter: About 4.7 cm. Receptacle height: About 1 cm. Receptacle diameter: About 9 mm. Receptacle color: Close to NN155A.

*Ray florets.*—Length: About 3.5 cm. Width: About 8 mm. Shape: Narrowly oblanceolate. Apex: Praemorse to emarginate. Base: Cuneate. Margin: Entire. Texture, upper and lower surfaces: Smooth, glabrous; longitudinally ridged. Number of ray florets per inflorescence: About 18 arranged in a single whorl. Aspect: About 30° from horizontal. Color: When opening, upper surface: Close to 35A. When opening, lower surface: Close to 51B. Fully opened, upper surface: Close to 51A and 184C to 184D; with development, color becoming closer to 182D, towards the base, close to 151D. Fully opened, lower surface: Close to 184C to 184D; with development, color becoming closer to 180C tinged with close to 151D.

*Disc florets.*—Length: About 2.4 cm. Diameter: About 5 mm. Shape: Tubular, enlarged; apices praemorse. Number of disc florets per inflorescence: About 200. Texture, upper and lower surfaces: Smooth, glabrous. Color: Immature, inner surface: Close to 32A to 32B; towards the base, close to 21C. Immature, outer surface: Close to 47B; towards the base, close to 11B to 11C. Mature, inner surface: Close to 51A and 184C to 184D. Mature, outer surface: Close to 184C to 184D.

*Receptacle spines.*—Quantity: One per disc floret. Shape: Acicular. Apex: Acute. Base: Attenuate. Texture: Smooth, glabrous. Color: Apex: Close to 45A. Mid-section: Close to 143A to 143B. Base: Close to 145D.

*Involucral bracts.*—Quantity per inflorescence: About 60 in about three whorls. Length: About 1 cm. Width: About 4 mm. Shape: Ovate. Apex: Acute. Base: Cuneate. Margin: Entire. Texture, upper surface: Smooth, glabrous. Texture, lower surface: Sparsely pubescent along the margins. Color, upper surface: Close to 143C. Color, lower surface: Close to 143B.

*Peduncles.*—Length, terminal peduncle: About 7 cm. Diameter: About 4 mm. Strength: Strong. Aspect: Mostly upright. Texture: Pubescent, strigose. Color: Close to 146C to 146D tinged with close to 183A and 184A.

*Reproductive organs.*—Androecium (present on ray and disc florets): Quantity per floret: About two. Filament length: About 2 mm. Filament color: Close to N155B to N155C. Anther shape: Oblong, short. Anther length: About 1 mm. Anther color: Close to N199B. Pollen amount: None observed. Gynoecium (present only on disc florets): Quantity per floret: One. Pistil length: About 3 mm. Stigma shape: Decurrent. Stigma color: Close to 1B. Style length: About 2 mm. Style color: Close to 154C. Ovary color: Close to 157A to 157B. Fruits/seeds: Fruit and seed development have not been observed.

Disease/pest resistance: Plants of the new *Echinacea* have not been shown to be resistant to pathogens and pests common to *Echinacea.*

Garden performance: Plants of the new *Echinacea* have exhibited good tolerance to rain and wind and have been observed to tolerate high temperatures of about 35° C. and hardy to USDA Hardiness Zone 4.

It is claimed:

1. A new and distinct *Echinacea* plant named 'Raspberry Truffle' as illustrated and described.

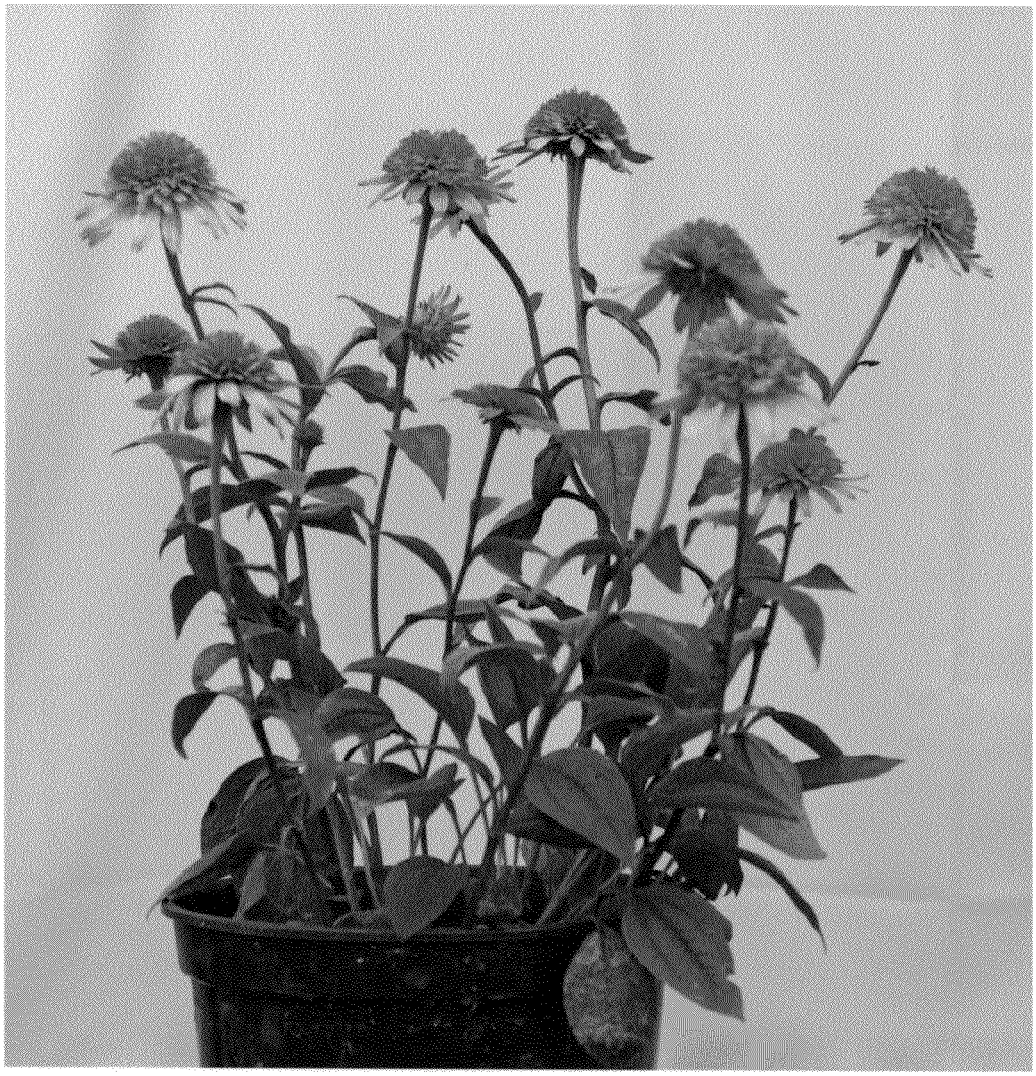

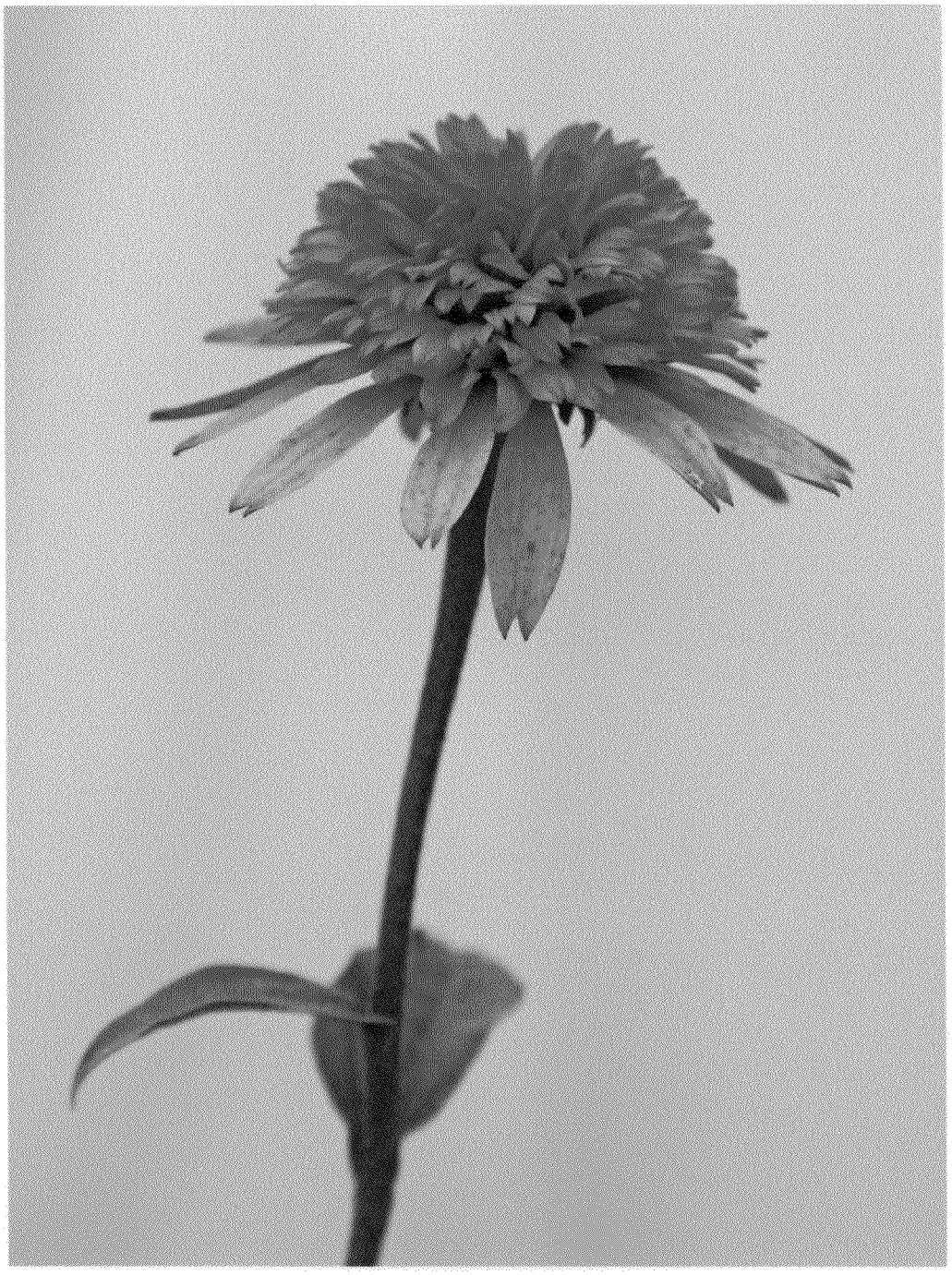

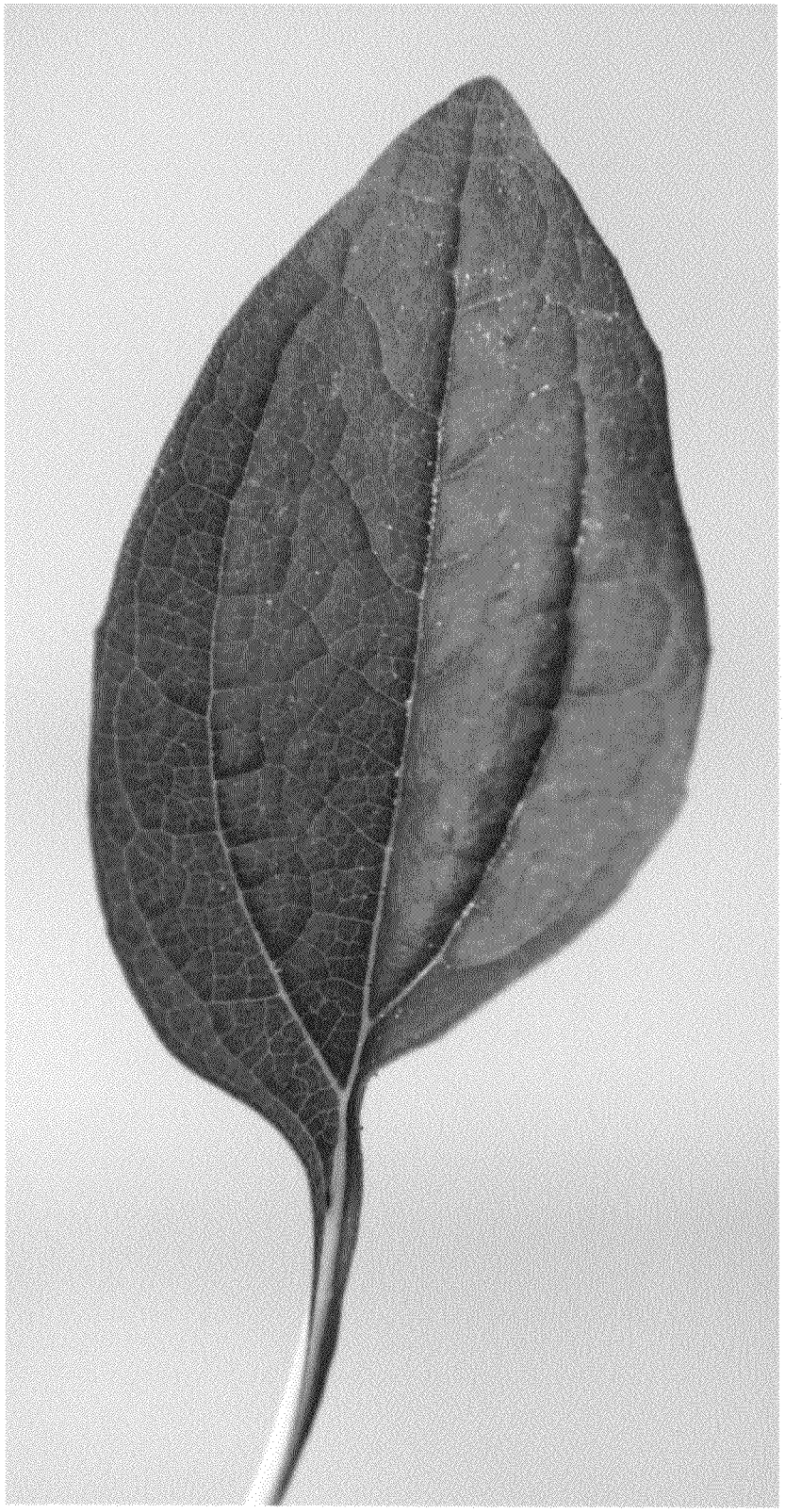

* * * * *